United States Patent
Atwood

(10) Patent No.: US 7,166,591 B1
(45) Date of Patent: Jan. 23, 2007

(54) CATALYTIC CLEAVAGE OF PHOSPHATE ESTER BONDS BY BORON CHELATES

(75) Inventor: David Allan Atwood, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/774,619

(22) Filed: Feb. 9, 2004

Related U.S. Application Data

(60) Provisional application No. 60/445,985, filed on Feb. 7, 2003.

(51) Int. Cl.
*A61K 31/555* (2006.01)
(52) U.S. Cl. .......................... 514/230.5; 544/69; 549/4
(58) Field of Classification Search .................. 544/69; 514/230.5; 549/4
See application file for complete search history.

(56) References Cited

OTHER PUBLICATIONS

Keizer et al., Canadian J. Chem, (2002), vol. 80, No. 11, p. 1463-68.*
David et al. Accelerated hydrolysis of industrial organophosphates in water and soil using sodium perborate. Environmental Pollution. vol. 105. 1999. pp. 121-128.
Wei et al. Chelated Borates: Synthesis, reactivity, and cation formation. Inorg. Chem. vol. 37. 1998. pp. 4934-4938.
Wei et al. Synthesis and Structures of Salen-Supported Borates Containing Siloxides. Inorg. Chem. vol. 38. 1999. pp. 3914-3918.
Brown et al. An intramolecularly Stabilized Arylboron Dibromide. Heteroatom Chemistry. vol. 9. No. 1. 1998. pp. 79-83.
Yang et al. Chemical detoxification of Nerve Agent VX. Acc. Chem. Res. vol. 32. 1999. pp. 109-115.
Blasko et al. Recent Studies of Nucleophilic General-Acid, and Metal Ion Catalysis of Phosphate Diester Hydrolysis. Acc. Chem. res. vol. 32. 1999. pp. 475-484.
Oivanen et al. Kinetics and Mechanisms for the cleavage and Isomerization of the Phosphodiester bonds of RNA by bronsted acids and Bases. Chem. Rev. vol. 87. 1998. pp. 961-990.
Gajda et al. Highly efficient phosphodiester hydrolysis promoted by dinuclear copper (II) complex. Inorg. Chem. vol. 40. 2001. pp. 4918-4927.
Jones et al. Enhanced base hydrolysis of coordinated phosphate esters: the reactivity of an unusual cobalt (III) amine dimer. J. Am. Chem. Soc. 1984. vol. 106. pp. 7807-7819.
Vance et al. Functional group convergency in a binuclear dephosphorylation reagent. J. Ame. Chem. Soc. vol. 115. 1993. pp. 12165-12166.
McCue et al. Hydrolysis of a model for the 5'-cap pf mRNA by dinuclear copper (II) and Zinc (II) Complexes. Rapid hydrolysis by four copper (II) ions. Inorg. Chem. vol. 38. 1999. pp. 6136-6142.
Scrimin et al. Comparative reactivities of phosphate ester cleavages by metallomicelles. Langmuir. vol. 12. 1996. pp. 6235-6241.
Yamami et al. Macrocyclic heterodinuclear ZnIIPbII complexes: synthesis, structures, and hydrolytic function toward Tris (p-nitrophenyl) phosphate. Inorg. Chem. 1998. vol. 37. pp. 6832-6838.
Kaminskaia et al. Reactivity of u-hydroxodizinc (II) centers in enzymatic catalysis through model studies. Inorg. Chem. vol. 39. 2000. pp. 3365-3373.
Chapman et al. Selective hydrolysis of phosphate esters, nitrophenyl phosphates and UpU, by dimetric zinc complexes depends on the spacer length. J. Ame. Chem. Soc. 1995. vol. 117. pp. 5462-5469.
Molenveld et al. Highly efficient phosphate diester transesterification by a Calix [4] arene-based dinuclear zinc (II) catalyst. J. Am. Chem. Soc. vol. 119. 1997. pp. 2948-2949.
Benton et al. The cleavage of ethers with boron bromide. I. Some common ether. J. Am/ Chem. Soc. vol. 64. 1942. pp. 1128-1129.
Kim et al. Direct conversion of silyl ethers into alkyl bromides with boron tribromide. J. Org. Chem. vol. 53. 1988. pp. 3111-3113.
Bazzicalupi et al. Carboxy and diphosphate ester hydrolysis by a dizinc complex with a new alcohol-pendant macrocycle. Inorg. Chem. 1999. vol. 38. pp. 4115-4122.
Ember Lois. EPA Destroying chemical arms:No easy task. C & EN. Aug. 30, 1999. pp. 11-12.
Ranu et al. Dealkylation of ethers. A review. Organic preparations and procedures int. vol. 28. No. 4. pp. 371-409.
Miguel-Angel Munoz-Hernandez et al., "Reactivity and Derivitization of Five-Coordinate, Chelated Aluminum," Inorg. Chem, 2001, 40, 6782-6787.
Y. Wang et al., "Ligand-Tetrahydrofuran Coupling in Chelated Aluminum Phosphinates," Inorg. Chem. 2002, 41, 558-565.
Yuzhong Wang et al., "Five-Coordinate Organoaluminum Acetylides and Crystal Structure of the Hydrosylate, [Salophen (tBu)Al]2O," Journal of Organometallic Chemistry 689 (2004). 759-765.
David, Michael D. et al., Accelerated hydrolysis of industrial organophosphates in water and soil using sodium perborate; Environ. Pollution 105 (1999) 121-128.
Olivanen, Mikko et al., Kinetics and Mechanisms for the Cleavage and Isomerization of the Phosphodiester Bonds of RNA by Bronsted Acids and Bases; Chem. Rev. 1998, 98, 961-990.
Blasko, Andrei et al., Recent Studies of Nucleophilic, General-Acid, and Metal Ion Catalysis of Phosphate Diester Hydrolysis; Acc. Chem. Res. 1999, 32, 475-484.

(Continued)

*Primary Examiner*—Taofiq Solola
(74) *Attorney, Agent, or Firm*—King & Schickli, PLLC

(57) ABSTRACT

Novel chemical compounds are disclosed having the general formula $L\{YX_m\}_n$, wherein X is selected from the Group 13 elements, Y is a halide, and L is a chelating ligand containing at least one binding atom contacting the Group 13 element, the atom being selected from the group consisting of C, N, O, and S, and m and n are integers having a value of at least 1. L may be a Schiff base type ligand, such as a salen ligand. The compositions of the present invention may be bidentate, quadridentate, or greater. The compositions may be used in dealkylation of phosphate esters or ethers. Advantageously, the methods of the present invention may be rendered catalytic.

12 Claims, 5 Drawing Sheets

OTHER PUBLICATIONS

Bazzicalupi, Carla et al., Carboxy and Diphosphate Ester Hydrolysis by a Dizinc Complex with a New Alcohol-Pendant Macrocycle; Inorg. Chem. 1999, 38, 4115-4122.

Gajda, Tamas et al., Highly Efficient Phosphodiester Hydrolysis Promoted by a Dinuclear Copper (II) Complex; Inorg. Chem., 2001, 40, 4918-4927.

Jones, David R. et al., Enhanced Base Hydrolysis of Coordinated Phosphate Esters: The Reactivity of an Unusual Cobalt (III) Amine Dimer; J. Am. Chem. Soc. 1984, 106, 7807-7819.

Vance, David H. et al., Functional Group Convergency in a Binuclear Dephosphorylation Reagent; J. Am. Chem. Soc., 1993, 115, 12165-12166.

McCue, Kevin P. et al., Hydrolysis of a Model for the 5'-Cap of mRNA by Dinuclear Copper (II) and Zinc (II) Complexes . . . Rapid Hydrolysis by Four Copper (II) Ions; Inorg. Chem. 1999, 38, 6136-6142.

Scrimin, Paolo et al., Comparative Reactivities of Phosphate Ester Cleavages by Metallomicelles, Langmuir 1996, 12, 6235-6241.

Kaminskaia, Natalia V., et al., Reactivity of u-Hydroxodizinc (II) Centers in Enzymatic Catalysts through Model Studies; Inorg. Chem. 2000, 39, 3365-3373.

Yamami, Masako et al., Macrocyclic Heterodinuclear ZnIIPbII Complexes: Synthesis, Structures and Hydrolytic Function toward Tris(p-nitrophenyl) Phosphate; Inorg. Chem. 1998, 37, 6832-6838.

Chapman, William H. Jr. et al., Selective Hydrolysis of Phosphate Esters, Nitrophenyl Phosphates and UpU, by Dimeric Zinc Complexes Depends on the Spacer Length; J. Am. Chem. Soc. 1995, 117, 5462-5469.

Molenveld, Peter et al., Highly Efficient Phosphate Diester Transesterification by a Calix[4]arene-Based Dinuclear Zinc(II) Catalyst;J. Am. Chem. Soc. 1997, 119, 2948-2949.

Benton, F.L. et al., The Cleavage of Ethers with Boron Bromide; Contrib. from Chemical Labs of U. of Notre Dame, May 1942; vol. 64 p. 1128.

Kim, Sunggak et al., Direct Conversion of Silyl Ethers into Alkyl Bromides with Boron Tribromide, J. Org. Chem. 1988, 53, 3111-3113.

Wei, Pingrong et al., Synthesis and Structure of Salen-Supported Borates Containing Siloxides, Inorg. Chem. 1999, 38, 3914-3918.

Brown, David S., An Intramolecularly Stabilized Arylboron Dibromide, Heteroatom Chem. vol. 9, No. 1, 1998, 79-83.

Yang, Yu-Chu, Chemical Detoxification of Nerve Agent VX, Acc. Chem. Res. 1999, 32, 109-115.

Ember, Lois, Destroying chemical arms: No easy task, C&EN Aug. 30, 1999, 11.

Hileman, bette, EPA Cuts Use of Common Pesticide, C&EN Jun. 12, 2000, 11.

Goodman, Steven N. et al., A Practical Synthesis of a,B-Unsaturated Imides, Useful Substrates For Asymmetric Conjugate Addition Reactions, Adv. Synth. Catal. 2002, 344, No. 9.

* cited by examiner

CATALYTIC CLEAVAGE OF PHOSPHATE ESTER BONDS BY BORON CHELATES

This application claims the benefit of U.S. Provisional Patent Application Ser. No. 60/445,985 filed Feb. 7, 2003.

This invention was made with partial Government support under NSF CAREER award CHE 9816155. The Government may have certain rights in this invention.

TECHNICAL FIELD

The present invention relates to compositions and methods for cleavage of phosphate ester and ether bonds. In particular, the invention relates to a chelating ligand comprising a Group 13 element and a halide, and to methods for using the ligand for dealkylation of a phosphate ester or an ether.

BACKGROUND OF THE INVENTION

It is known that the breaking of a phosphate ester bond is an important step in the destruction of chemical warfare agents such as Sarin gas and VX, in the destruction of pesticides such as chloropyrifos, and in other biological systems. Such compounds irreversibly block a serine hydroxy group in the cellular enzyme acetylcholinesterase by phosphorylation, thereby disrupting the cells' neurological function. Accordingly, substantial effort has been devoted to development of methods for decontamination of such nerve agents and pesticides. The cleavage of the P—O—C bond in such nerve agents/pesticides has been targeted as a method of decontamination. Many such methods use d-block metals such as cobalt, copper, and zinc. It is also known to destroy nerve agents by hydrolyzing them using basic solutions and/or bleach to oxidize them to less toxic inorganic phosphates and alkali. However, these solutions are caustic and should only be handled under carefully controlled conditions. Large excesses of bleach and/or bases are required for successful decontamination, and the active agent (chlorine) in bleach decreases with time. Further, bases and bleach are not selective for nerve agents, and readily undergo undesirable and potentially explosive side reactions.

Similarly, methods are known for breaking the C—O—C bond in ethers such as methyl tertiary butyl ether (MTBE) to prevent, for example, contamination of groundwater thereby. Prior art methods include cleavage by hydrogen halides, organic acids, amines/amine salts, sulfonyl halides, inorganic acid anhydrides, Lewis acid halides, Grignard reagents, and alkali metal alkyls. The modes of action of these reagents are varied, including elimination, substitution, and oxidative cleavage. Further, it is known to cleave MTBE by concentrated acid. However, concentrated acid also risks contamination of the environment, and the rate of hydrolysis is slow when dilute aqueous acid is used to avoid contamination. Biodegradation of MTBE is slow under anaerobic and aerobic conditions using conventional methodology, and certain methods such as gas phase catalytic oxidation of MTBE require high temperatures.

There is accordingly identified a need in the art for a successful deactivating/destroying agent for such toxic nerve agents as nerve gas (Sarin gas, VX, and the like) and organophosphate pesticides. Such an agent should be easily synthesized from inexpensive reagents, should be soluble in the same solvents as the nerve gases/pesticides, will preferably be selective for the nerve agents, will not readily undergo unwanted side effects upon reaction with the nerve agents, and will be substantially non-toxic.

SUMMARY OF THE INVENTION

In accordance with the foregoing, a new class of chelating ligands have been synthesized which serve as catalysts for the dealkylation of phosphate ester and ether bonds. Each ligand comprises a Group 13 element and a halide. While not wishing to be bound by any theory, when combined with a molecule containing a phosphate ester bond or an ether bond, it is believed that the ligand undergoes dissociation of a halide which then attacks a carbon atom of the bond being broken, thereby cleaving the bond.

In one aspect of the invention a chemical compound is provided, comprising the general formula $L\{YX_m\}_n$. Y may be selected from the Group 13 elements consisting of boron, aluminum, gallium, indium, and tellurium. X may be selected from the halide group consisting of fluorine, chlorine, bromine, iodine, and astatine. L is typically a chelating ligand containing at least one binding atom contacting the Group 13 element, the atom selected from the group consisting of C, N, O, and S, and m and n are integers having a value of at least 1.

In another aspect, L may be a Schiff base-containing ligand. Y may be selected from the Group 13 elements consisting of boron, aluminum, gallium, indium, and tellurium, and X may be selected from the halide group consisting of fluorine, chlorine, bromine, iodine, and astatine. In one embodiment, L may be a salen ligand which is bidentate, quadridentate, or greater. Typically, L is selected from the group consisting of Salen ($^t$Bu), Salpen ($^t$Bu), Salben ($^t$Bu), and Salhen ($^t$Bu). The general formula of the chemical compound may be:

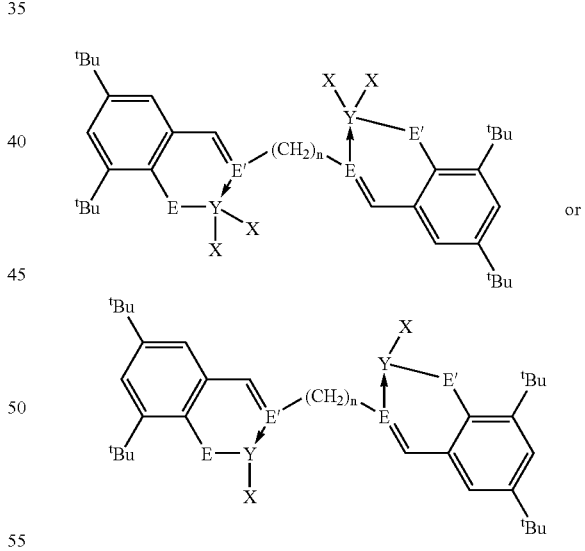

In yet another aspect, a method is provided for dealkylation of a phosphate ester or an ether, comprising contacting the phosphate ester or ether with a compound comprising the general formula $L\{YX_m\}_n$ as described above. As described, L is typically a salen ligand, Y is typically boron or aluminum, and X is typically chlorine, bromine, or iodine.

In still yet another aspect of the present invention, a catalytic method for dealkylation of a phosphate ester or an ether, comprising contacting the phosphate ester or ether with the compositions as described above in the presence of $BBr_3$. The phosphate ester or ether and $BBr_3$ may be added in equimolar amounts. Typically, the dealkylation reaction using the compositions and methods of the present invention is conducted at ambient temperature. Addition of an excess of $BBr_3$ renders the reaction catalytic, allowing regeneration of the original composition and continuation of the reaction.

Yet still further, the present invention provides a catalytic method for dealkylation of a phosphate ester or an ether, comprising contacting the phosphate ester or ether with a compound comprising the general formula $L\{YX_m\}_n$ wherein Y is selected from the Group 13 elements consisting of boron, aluminum, gallium, indium, and tellurium, X is selected from the halide group consisting of fluorine, chlorine, bromine, iodine, and astatine, L is a chelating ligand containing at least two molecules E and E' contacting the Group 13 element, the molecules E and E' being selected from the group consisting of C, N, O, and S, and m and n are integers having a value of at least 1. Typically, the compound generates a cationic intermediate upon contacting the phosphate ester or ether, the cationic intermediate having the general formula:

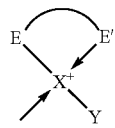

As describing above, L may be a Schiff base-containing ligand, such as a salen ligand. L may be a bidentate ligand, a quadridentate ligand, or greater. In one embodiment, L is selected from the group consisting of Salen (ʹBu), Salpen (ʹBu), Salben (ʹBu), and Salhen (ʹBu). The reaction is rendering catalytic by conducting it in the presence of $BBr_3$. The phosphate ester or ether and $BBr_3$ may be added in equimolar amounts. The dealkylation reaction may be conducted at ambient temperature.

Other objects of the present invention will become apparent to those skilled in this art from the following description wherein there is shown and described a preferred embodiment of this invention, simply by way of illustration of the modes currently best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawings incorporated in and forming a part of the specification illustrates several aspects of the present invention and, together with the description, serves to explain the principles of the invention. In the drawing.

Reference will now be made in detail to the presently preferred embodiments of the invention, examples of which are illustrated in the accompanying drawings.

DETAILED DESCRIPTION OF THE INVENTION

Figure 1:
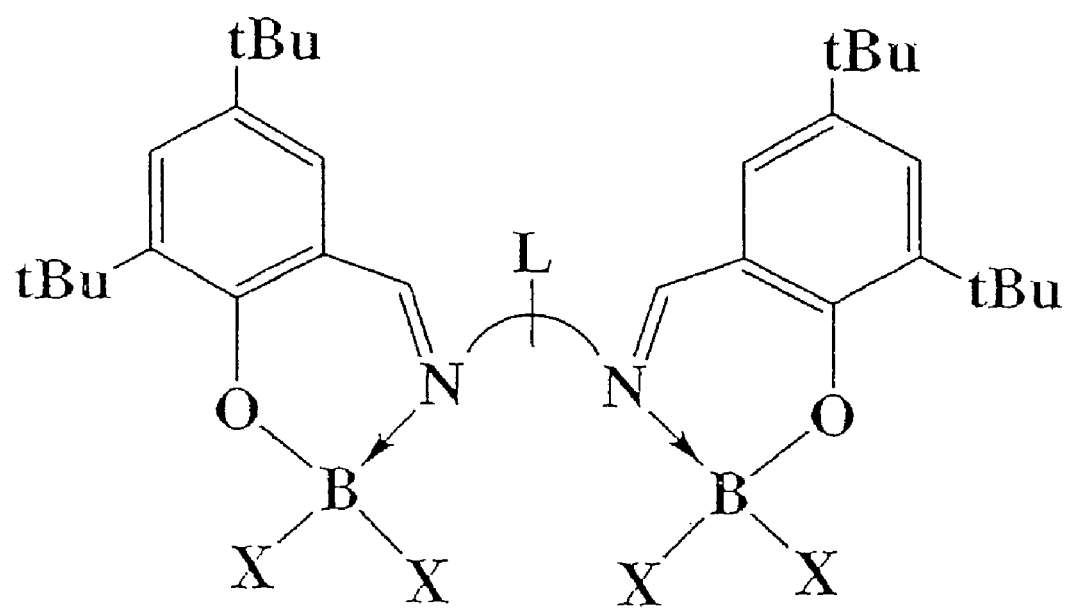
FIG. 1 is a structural depiction of a bidentate ligand according to the present invention, wherein X is a halide.
Figure 2:
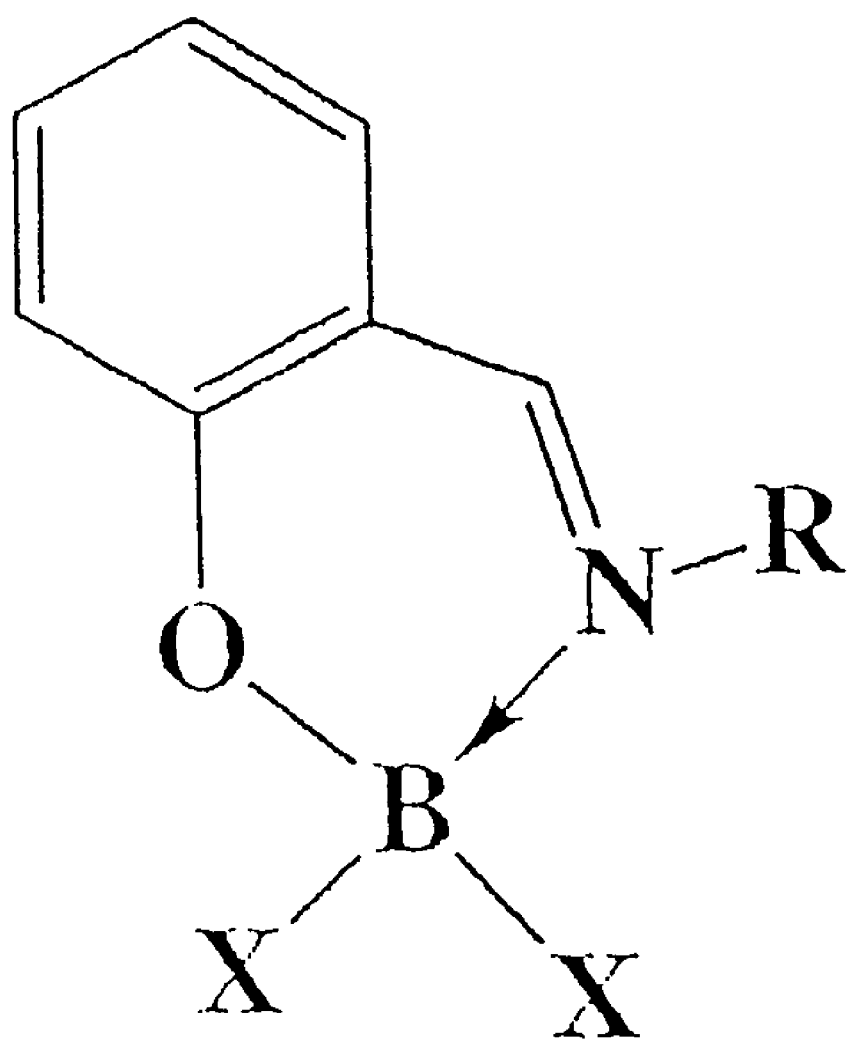
FIG. 2 is a structural depiction of a quadridentate ligand according to the present invention, wherein X is a halide and L is a quadridentate Schiff base ligand.
Figure 3:
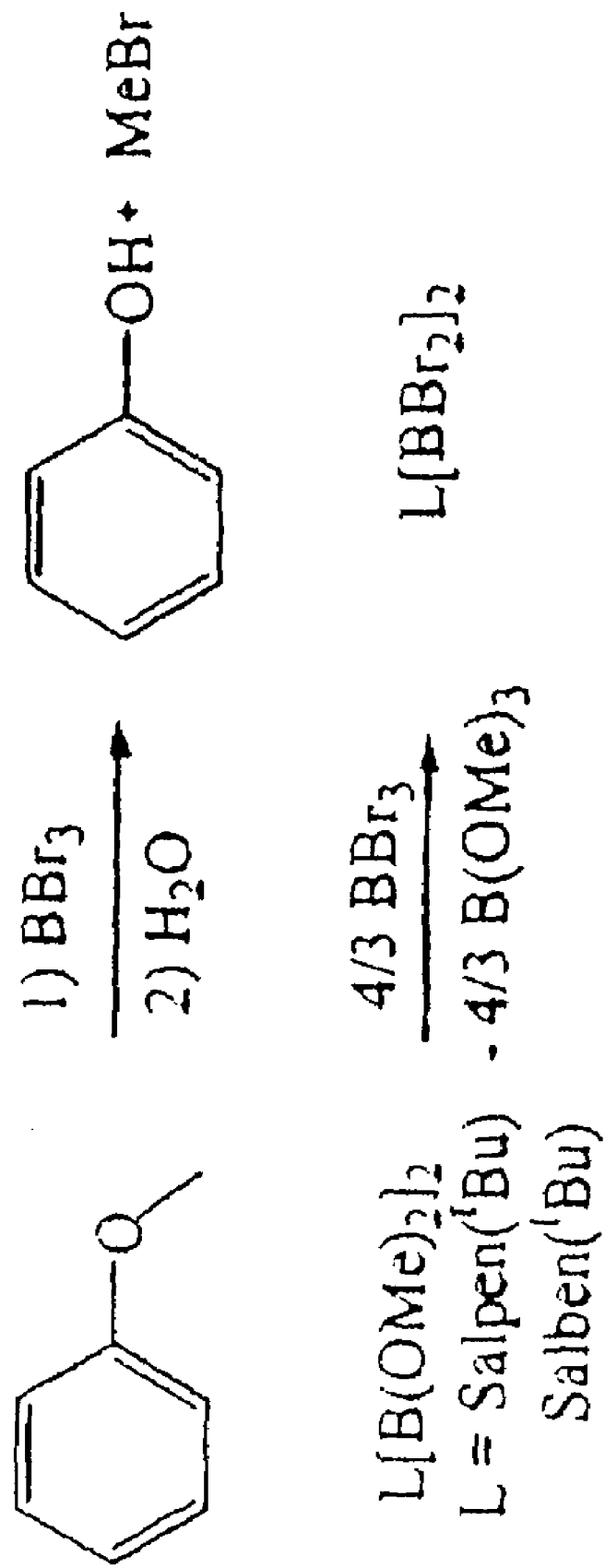
FIG. 3 schematically depicts preparation of a bidentate ligand according to the present invention by combining Salpen(ʹBu)[B(OMe)₂]₂ (1) and Salben(ʹBu)[B(OMe)₂]₂ (2) with a stoichiometric amount of $BBr_3$.

In accordance with one aspect of the present invention, the composition provided by the present invention may be a chelate having the general formula $L\{YX_m\}_n$, where Y is a Group 13 element, X is a halide, and L is chelating ligand having a bidentate binding site comprising sites E and E' contacting the Group 13 element. E and E' may be O, N, P, S, or any combination thereof. Both bidentate (FIG. 1), quadridentate (FIG. 2), and greater ligands are contemplated by the present invention. The compositions of the present invention show excellent activity in dealkylating various phosphates and ethers as will be shown herein. An additional advantage is that the method of the present invention may be conducted at room temperature.

In one embodiment, the present invention provides a chemical compound comprising a chelating ligand L which is a salen ligand, which may have the general formula:

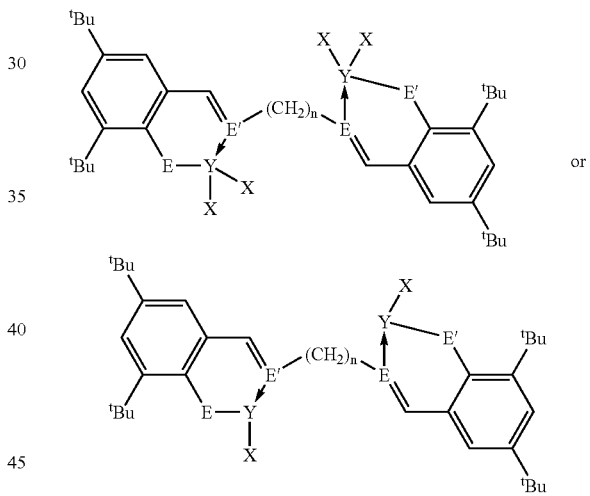

As discussed previously, Y may be selected from the Group 13 elements consisting of boron, aluminum, gallium, indium, tellurium, and any combination thereof. X may be selected from the halide group consisting of fluorine, chlorine, bromine, iodine, astatine, and any combination thereof. E and E' may be selected from the group consisting of C, N, O, S, and any combination thereof, and n is an integer having a value of at least 1.

Other aspects of the present invention will become apparent to those skilled in this art from the following description wherein there is shown and described a preferred embodiment of this invention, simply by way of illustration of one of the modes best suited to carry out the invention. As it will be realized, this invention is capable of other different embodiments and its several details are capable of modification in various, obvious aspects all without departing from the intended scope of the invention. Accordingly, the descriptions and examples herein will be regarded as illustrative in nature and not as restrictive.

EXAMPLE 1

Preparation of Salpen($^t$Bu)(BBr$_2$)$_2$

Binuclear boron bromides were prepared in high yields by combining Salpen($^t$Bu)[B(OMe)$_2$]$_2$ or Salben($^t$Bu)[B(OMe)$_2$]$_2$ with a stoichiometric amount of BBr$_3$. To a stirring solution of Salpen($^t$Bu)[B(OMe)$_2$]$_2$ (3.0 g, 4.62 mmol) in toluene (50 ml) was added 1 M BBr$_3$ in heptane (6.24 ml, 6.24 mmol). The reaction mixture was stirred for 24 hours, and the solvent removed. The remaining solid was washed with 10 ml of hexanes, and filtration and vacuum drying yielded 3.28 g (88% yield) Salpen($^t$Bu)(BBr$_2$)$_2$.

EXAMPLE 2

Preparation of Salben($^t$Bu)(BBr$_2$)$_2$

To a stirring solution of Salben($^t$Bu)[B(OMe)$_2$]$_2$ (1.0 g, 1.51 mmol) in toluene (50 ml) was added 1 M BBr$_3$ in heptane (2.04 ml, 2.04 mmol). The reaction mixture was stirred for 18 hours at room temperature. The solution was concentrated to 10 ml, filtered, and dried. The yield was 0.96 g (76% yield) Salben($^t$Bu)(BBr$_2$)$_2$.

NMR analysis showed a broad single peak (at δ −0.57 and −0.40 ppm, respectively) for both binuclear boron bromide compounds prepared as described in Examples 1 and 2, upfield from a related chloride analogue Salpen($^t$Bu)[BCl$_2$]$_2$ (at δ 6.21 ppm).

EXAMPLE 3

Dealkylation of Phosphates with Salpen($^t$Bu)(BBr$_2$)$_2$

Salpen($^t$Bu)(BBr$_2$)$_2$, prepared as described in Example 1, was evaluated for its ability to dealkylate various phosphate esters. In a NMR tube, phosphate was added to an equimolar solution of Salpen($^t$Bu)(BBr$_2$)$_2$ in CDCl$_3$ and held at room temperature for 30 minutes. The reaction was monitored by $^1$H NMR. As shown in Table 1, significant dealkylation, measured by the amount of phosphate remaining in the reaction mixture in comparison to the amount of alkyl bromide produced, could be achieved with the composition of the present invention.

TABLE 1

Percent dealkylation of phosphates with Salpen($^t$Bu)(BBr$_2$)$_2$

| Phosphate | Conversion (%)[a] |
|---|---|
| (MeO)$_3$P(O) | 89 |
| (EtO)$_3$P(O) | 63 |
| ($^n$BuO)$_3$P(O) | 99 |
| ($^n$PentO)$_3$P(O) | 98 |
| (MeO)$_2$P(O)H | 85 |
| (MeO)$_2$P(O)Me | 99 |
| ($^i$PrO)$_2$P(O)H | 63 |
| (PhO)$_2$((2-Et)HexO)P(O) | 71 |
| (Me$_3$SiO)$_3$P(O) | 98 |
| (PhO)$_3$P(O) | 0 |

[a]The percent conversion was determined by the amount of phosphate remaining to the amount of alkyl bromide produced in the $^1$H NMR.

EXAMPLE 4

Dealkylation of Phosphates with Binuclear Boron Compounds

Various binuclear boron compounds, synthesized substantially as described in Examples 1 and 2, were evaluated for dealkylation of phosphate esters as described in Example 3. For comparison, a positive control consisting of BBr$_3$ in CDCl$_3$ was used. As shown in Tables 2–5, the compounds of the present invention were effective in cleaving phosphate bonds for various phosphate compounds. In contrast, BBr$_3$ was ineffective (Table 5). Activity of the boron halide compounds of the present invention did not decrease with extension of the alkyl chain on the phosphates. However, a slight decrease in activity of the compounds was observed with the branched phosphates such as (PhO)$_2$((2-Et)HexO)P(O).

TABLE 2

Dealkylation of phosphates by Salen ligands having the formula L[BBr$_2$]$_2$.

| | Phosphate | | | | | | | | | | |
|---|---|---|---|---|---|---|---|---|---|---|---|
| | (MeO)$_3$P(O) | | (EtO)$_3$P(O) | | (n-BuO)$_3$P(O) | | (MeO)$_2$P(O)Me | | (PhO)$_2$P(O) (2-ethylhexyl) | | (MeSiO)$_3$P(O) | |
| L[BBr$_2$]$_2$ | 30 min. | 24 hr. | 30 min. | 24 hr. | 30 min. | 24 hr. | 30 min. | 24 hr. | 30 min. | 24 hr. | 30 min. | 24 hr. |
| Salen(t) | 76 | 94 | 26 | 32 | 42 | 57 | 61 | 77 | 48 | 58 | 88 | 89 |
| Salpen(t) | 74 | 82 | 68 | 74 | 99 | 99 | 84 | 99 | 75 | 83 | 98 | 98 |
| Salben(t) | 60 | 78 | 46 | 53 | 77 | 91 | 87 | 92 | 64 | 81 | 90 | 96 |
| Salhen(t) | 58 | 81 | 55 | 66 | 60 | 69 | 37 | 47 | 88 | 93 | 79 | 79 |

TABLE 3

Dealkylation of phosphates by Salen ligands having the formula L[MePhBBr$_2$]$_2$.

| | Phosphate | | | | | | | | | | | | | | |
|---|---|---|---|---|---|---|---|---|---|---|---|---|---|---|---|
| | (MeO)$_3$P(O) | | (EtO)$_3$P(O) | | (n-BuO)$_3$P(O) | | (MeO)$_2$P(O)H | | (MeO)$_2$P(O)Me | | (i-PrO)$_2$P(O)H | | (PhO)$_2$P(O) (2-ethylhexyl) | | (MeSiO)$_3$P(O) | |
| L[MePhBBr$_2$]$_2$ | 30 min. | 24 hr. | 30 min. | 24 hr. | 30 min. | 24 hr. | 30 min. | 24 hr. | 30 min. | 24 hr. | 30 min. | 24 hr. | 30 min. | 24 hr. | 30 min. | 24 hr. |
| Salen(t) | 45 | 62 | 40 | 98 | 31 | 46 | 59 | 67 | 47 | 56 | 42 | 74 | 12 | 32 | 43 | 45 |
| Salpen(t) | 52 | 69 | 50 | 64 | 58 | 75 | 67 | 82 | 64 | 69 | 32 | 65 | 46 | 67 | 48 | 63 |
| Salben(t) | 92 | 83 | 71 | 98 | 70 | 99 | 50 | 82 | 50 | 63 | 37 | 74 | 52 | 76 | 69 | 69 |
| Salhen(t) | 80 | 88 | 56 | 98 | 47 | 98 | 50 | 76 | 42 | 66 | 26 | 60 | 42 | 61 | 89 | 89 |

TABLE 4

Dealkylation of phosphates by Salen ligands having the formula L[BCl$_2$]$_2$.

Figure 5:
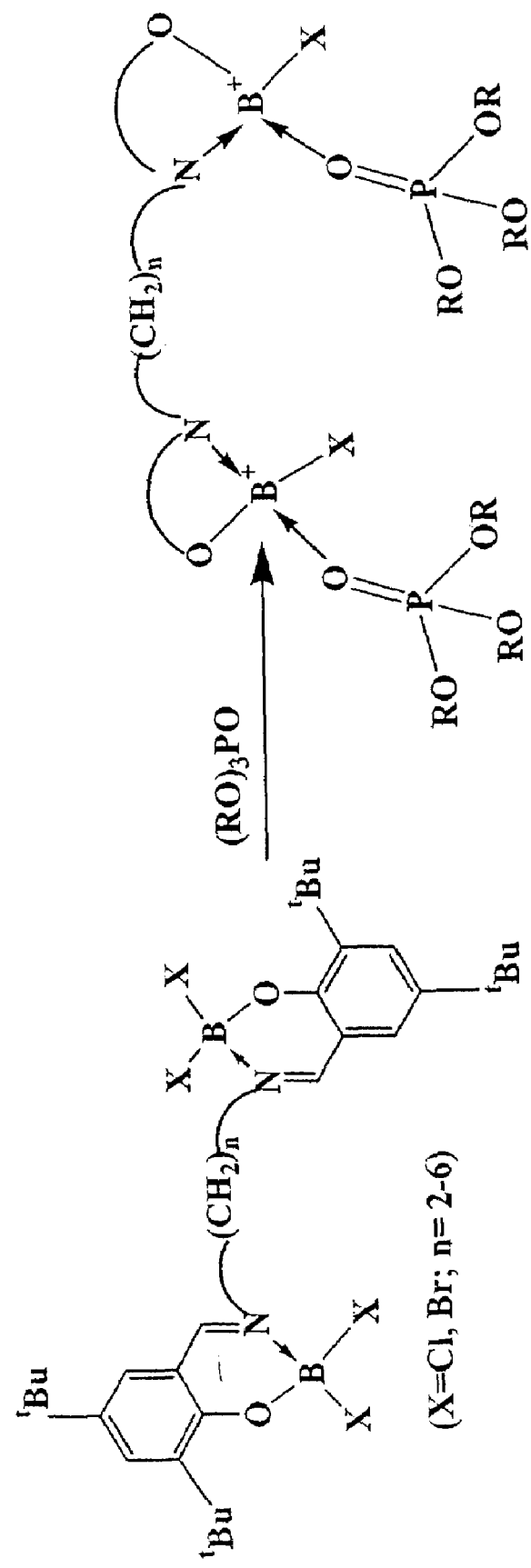
FIG. 5 schematically depicts the formation of a cationic intermediate from a composition of the present invention.

| | Phosphate | | | |
|---|---|---|---|---|
| | (MeO)$_3$P(O) | | (MeSiO)$_3$P(O) | |
| L[BCl$_2$]$_2$ | 30 min. | 24 hr. | 30 min. | 24 hr. |
| Salen(t) | 7 | 45 | 84 | 87 |
| Salpen(t) | 20 | 32 | 66 | 75 |
| Salben(t) | 11 | 53 | 81 | 84 |
| Salhen(t) | 7 | 47 | 57 | 63 |
| Salpten(t) | 42 | 62 | 73 | 86 | bond of a phosphate ester or ether, respectively, allowing a nucleophilic attack by the halide at the α-carbon. The reaction is depicted schematically in FIG. 5, using a phosphate ester and a binuclear boron compound according to the present invention as an example. Accordingly, the present invention contemplates use of such cationic intermediates for dealkylation of phosphate esters and ethers as described herein.

EXAMPLE 6

Cleavage of MTBE

Methyl tertiary butyl ether was added to a CDCl$_3$ solution of binuclear boron ligands synthesized substantially as described in Examples 1 and 2 (4:1 ratio of MTBE:ligand).

TABLE 5

Dealkylation of phosphates by BBr$_3$.

| | Phosphate | | | | | | | | | | | | | | | |
|---|---|---|---|---|---|---|---|---|---|---|---|---|---|---|---|---|
| | (MeO)$_3$P(O) | | (EtO)$_3$P(O) | | (n-BuO)$_3$P(O) | | (MeO)$_2$P(O)H | | (MeO)$_2$P(O)Me | | (i-PrO)$_2$P(O)H | | (PhO)$_2$P(O) (2-ethylhexyl) | | (MeSiO)$_3$P(O) | |
| | 30 min. | 24 hr. | 30 min. | 24 hr. | 30 min. | 24 hr. | 30 min. | 24 hr. | 30 min. | 24 hr. | 30 min. | 24 hr. | 30 min. | 24 hr. | 30 min. | 24 hr. |
| BBr$_3$ | 1.1 | 3.4 | 0 | 2.7 | 5 | 0 | 1 | 12 | 2 | 2 | 0 | 0 | 0 | 7 | 11 | 20 |
| B-Bromo | 74 | 99 | 37 | 66 | 31 | 54 | 84 | 87 | 58 | 92 | 76 | 84 | 87 | 95 | 99 | 99 |

[a]B-Bromocatecholborane

EXAMPLE 5

Catalytic Process for Dealkylating Phosphates

Figure 4:
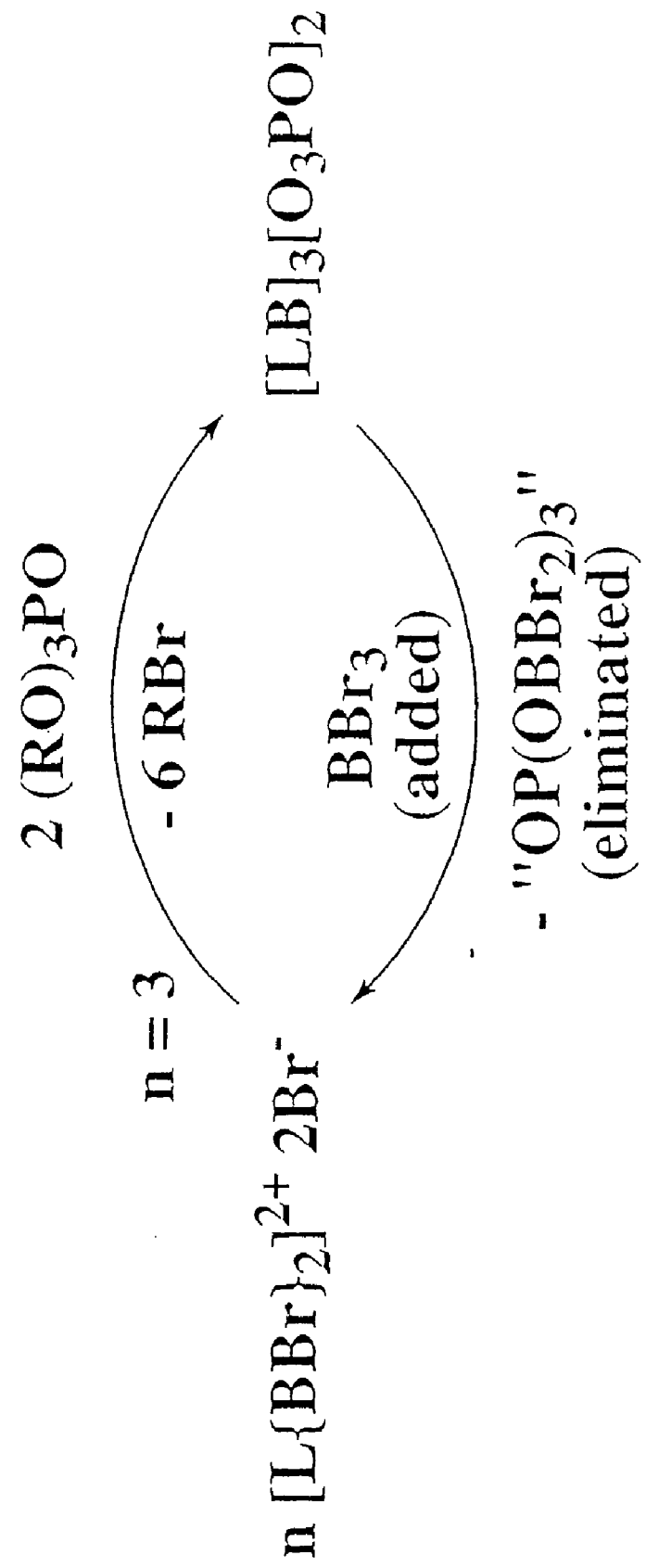
FIG. 4 graphically shows a catalytic process for dealkylation of a phosphate ester according to the present invention.

Because Salpen($^t$Bu)(BBr$_2$)$_2$ can be generated in situ from Salpen($^t$Bu)[B(OMe)$_2$]$_2$ and BBr$_3$, the process can be made catalytic. The reaction is shown schematically in FIG. 4. In a NMR tube, equimolar amounts of (MeO)$_3$P(O) and BBr$_3$ were added to a solution of Salpen($^t$Bu)(BBr$_2$)$_2$ in CDCl$_3$ in the ratio of 20:1 of phosphate to borate and held at room temperature. The reaction was monitored by $^1$H NMR. Dealkylation of trimethyl phosphate occurred within five minutes. Dealkylation (75% conversion) occurred within 30 minutes at a substrate to catalyst ratio of 200:1.

While not wishing to be bound by any theory, the mechanism may be one in which a cationic intermediate, which may be depicted in one embodiment of this invention as [(chelate)BBr]$^+$, coordinates the P—O—C or C—O—C The solution was held at room temperature, and the reaction monitored by $^1$H NMR. Percent dealkylation was monitored by comparing the amount of methyl bromide produced to the amount of trimethyl phosphate remaining. As shown in Table 6, the compositions of the present invention are capable of dealkylating ethers as well as phosphate esters.

TABLE 6

Cleavage of MTBE by bimetallic boron halide ligand.

| | Conversion (%)[a] | |
|---|---|---|
| Ligand | 30 min. | 24 hr. |
| Salen($^t$Bu)[BBr$_2$]$_2$ | 12 | 39.3 |
| Salpen($^t$Bu)[BBr$_2$]$_2$ | 3 | 10 |

TABLE 6-continued

Cleavage of MTBE by bimetallic boron halide ligand.

| | Conversion (%)[a] | |
|---|---|---|
| Ligand | 30 min. | 24 hr. |
| Salben(tBu)[BBr$_2$]$_2$ | 5 | 25 |
| Salhen(tBu)[BBr$_2$]$_2$ | 1 | 8 |

[a]Percent dealkylation was determined by comparing the amount of methyl bromide produced to the amount of trimethyl phosphate remaining in the $^1$H NMR.

The foregoing description is presented for purposes of illustration and description of the various aspects of the invention. The descriptions are not intended to be exhaustive or to limit the invention to the precise form disclosed. The embodiments described above were chosen to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A chemical compound having a chelating ligand L of the general formula:

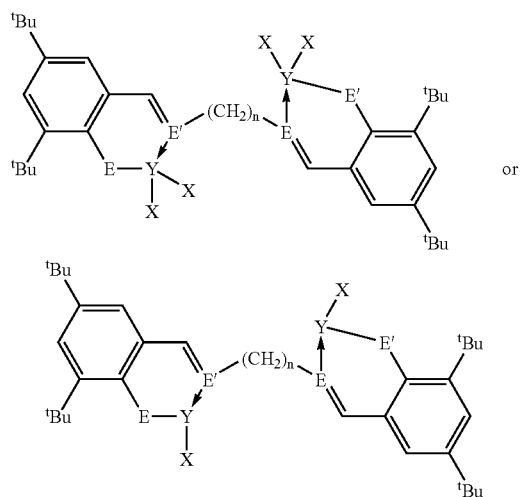

or wherein Y is selected from the Group 13 elements consisting of boron, aluminum, gallium, indium, and tellurium, X is selected from the halide group consisting of fluorine, chlorine, bromine, iodine, and astatine, E and E' are selected from the group consisting of C, N, O, and S, and n is an integer having a value of at least 1.

2. The chemical compound of claim 1, wherein L is selected from the group consisting of Salen (tBu), Salpen (tBu), Salben (tBu), and Salhen (tBu).

3. The chemical compound of claim 1, wherein Y is boron or aluminum.

4. The chemical compound of claim 1, wherein X is chlorine, bromine, or iodine.

5. The chemical compound of claim 1, wherein n is 2.

6. A composition comprising a chelating ligand L, the ligand having the general formula:

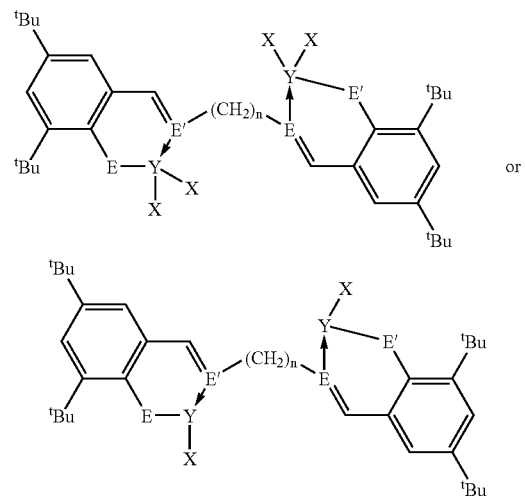

or wherein Y is selected from the Group 13 elements consisting of boron, aluminum, gallium, indium, and tellurium, X is selected from the halide group consisting of fluorine, chlorine, bromine, iodine, and astatine, E and E' are selected from the group consisting of C, N, O, and S, and n is an integer having a value of at least 1.

7. A method for dealkylation of a phosphate ester or an ether, comprising contacting the phosphate ester or ether with the chemical compound of claim 1.

8. The method of claim 7, wherein:

L is selected from the group consisting of Salen (tBu), Salpen (tBu), Salben (tBu), and Salhen (tBu);

Y is boron or aluminum;

X is chlorine, bromine, or iodine; and n is 2.

9. A catalytic method for dealkylation of a phosphate ester or an ether, comprising contacting the phosphate ester or ether with the chemical compound of claim 1 in the presence of BBr$_3$.

10. The method of claim 9, wherein:

L is selected from the group consisting of Salen (tBu), Salpen (tBu), Salben (tBu), and Salhen (tBu);

Y is boron or aluminum;

X is chlorine, bromine, or iodine; and n is 2.

11. The method of claim 9, wherein the phosphate ester or ether and BBr$_3$ are present in equimolar amounts.

12. The method of claim 9, wherein the dealkylation is conducted at ambient temperature.

* * * * *